(12) United States Patent
Kuroda et al.

(10) Patent No.: US 9,345,384 B2
(45) Date of Patent: May 24, 2016

(54) ENDOSCOPE HAVING BREAKABLE PORTIONS FOR PREVENTING DAMAGE TO THE IMAGING UNIT

(71) Applicant: OLYMPUS CORPORATION, Tokyo (JP)

(72) Inventors: Motohiro Kuroda, Hachioji (JP); Toru Shinmura, Hachioji (JP); Hiroaki Kagawa, Sagamihara (JP); Hiroyuki Nagamizu, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 169 days.

(21) Appl. No.: 13/740,591

(22) Filed: Jan. 14, 2013

(65) Prior Publication Data

US 2013/0131452 A1    May 23, 2013

Related U.S. Application Data

(63) Continuation of application No. PCT/JP2011/065190, filed on Jul. 1, 2011.

(30) Foreign Application Priority Data

Sep. 10, 2010   (JP) ................................. 2010-203507

(51) Int. Cl.
*A61B 1/00*        (2006.01)
*A61B 1/05*        (2006.01)
(Continued)

(52) U.S. Cl.
CPC ............ *A61B 1/00071* (2013.01); *A61B 1/0008* (2013.01); *A61B 1/00103* (2013.01); *A61B 1/05* (2013.01); *A61B 1/012* (2013.01); *A61B 1/018* (2013.01); *A61B 1/055* (2013.01)

(58) Field of Classification Search
CPC ....... A61B 1/00142; A61B 1/018; A61B 1/05

USPC ................... 600/10–136, 139–140, 146–147, 600/156–159
See application file for complete search history.

(56) References Cited

U.S. PATENT DOCUMENTS 7,150,713 B2 * 12/2006 Shener et al. ................. 600/156
2005/0085695 A1    4/2005 Shener et al.
(Continued)

FOREIGN PATENT DOCUMENTS

CN         101061940 A        10/2007
JP         08-140924          6/1996
(Continued)

OTHER PUBLICATIONS

JP 2010-7529 A and WO 2010/27109 A1, Yuichi et al., Apr. 8, 2010, Fujinon Corp.*
(Continued)

*Primary Examiner* — John P Leubecker
*Assistant Examiner* — Rajaa El Alami
(74) *Attorney, Agent, or Firm* — Scully, Scott, Murphy & Presser, P.C.

(57) ABSTRACT

An endoscope includes a first breakable portion provided between a part of an outer peripheral surface of a distal rigid section main body and a second inner peripheral surface, and including a fragile portion which is formed in a concaved-shape and which is more easy to break than any other part of the outer peripheral surface except for thereof. The endoscope includes a second breakable portion provided between a first inner peripheral surface and the second inner peripheral surface, and a third breakable portion provided between the first inner peripheral surface and a part of the outer peripheral surface of the distal rigid section main body, which differs from the fragile portion.

5 Claims, 12 Drawing Sheets

(51) Int. Cl.
    *A61B 1/012*     (2006.01)
    *A61B 1/018*     (2006.01)
    *A61B 1/055*     (2006.01)

(56) References Cited

U.S. PATENT DOCUMENTS

2006/0161046 A1    7/2006    Ouchi
2009/0221872 A1*    9/2009    Liddle et al. .................. 600/121

FOREIGN PATENT DOCUMENTS

| | | |
|---|---|---|
| JP | 10-85171 | 4/1998 |
| JP | 11-155805 | 6/1999 |
| JP | 2001-136421 | 5/2001 |
| JP | 2002-200034 | 7/2002 |
| JP | 2003-260029 | 9/2003 |
| JP | 2006-192090 | 7/2006 |
| JP | 2007-508871 | 4/2007 |
| JP | 2010-75269 | 4/2010 |
| JP | 2010075269 A * | 4/2010 |
| WO | 2010/027109 A1 | 3/2010 |

OTHER PUBLICATIONS

International Search Report dated Aug. 9, 2011 issued in PCT/JP2011/065190.

International Preliminary Report on Patentability together with the Written Opinion dated Apr. 18, 2013 received in related International Application No. PCT/JP2011/065190.

Notification of the First Office Action dated Jul. 30, 2014 from related Chinese Patent Application No. 201180037253.0, together with an English language translation.

* cited by examiner

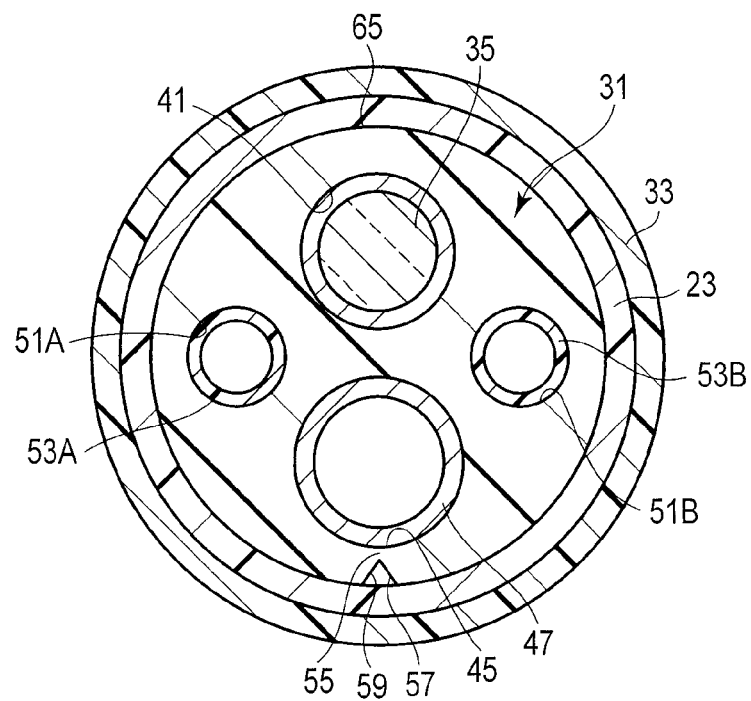
F I G. 3
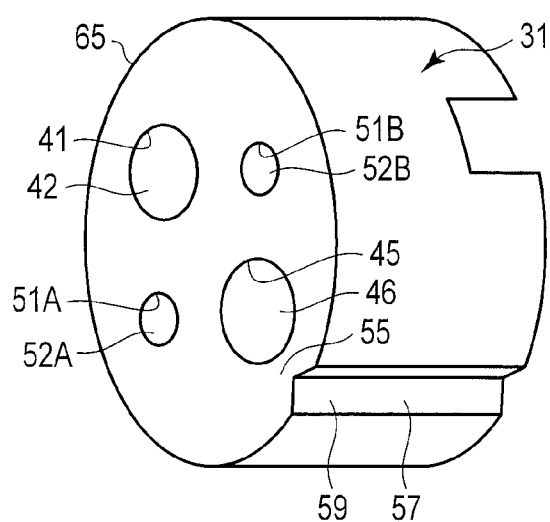
F I G. 4

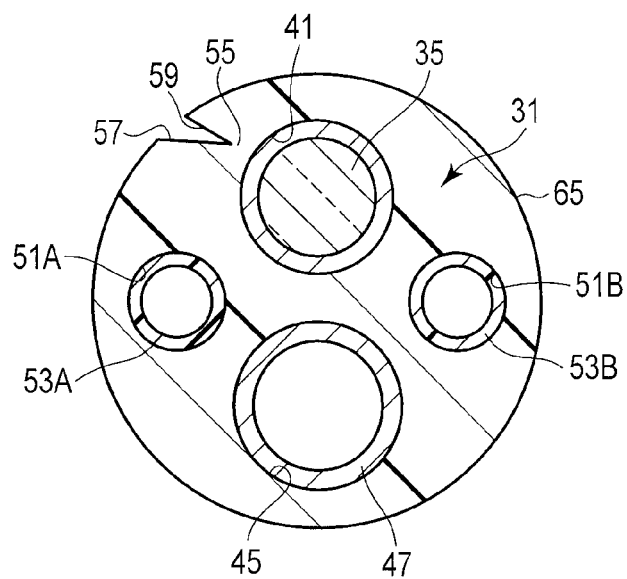
F I G. 7
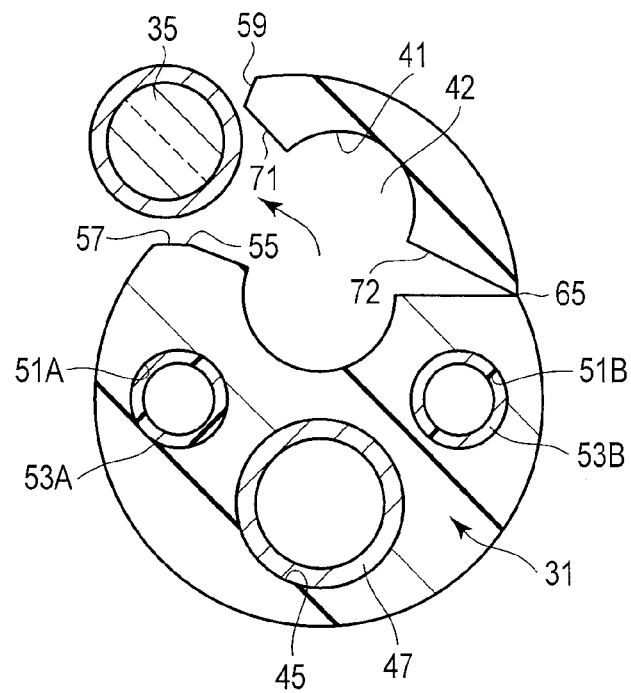
F I G. 8

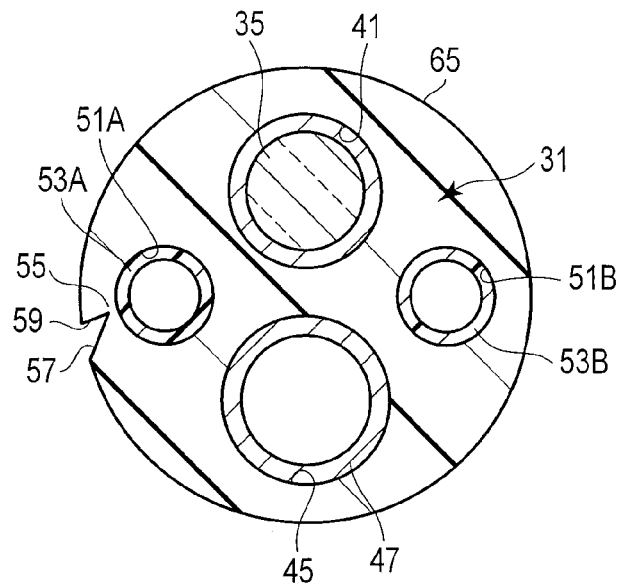
F I G. 9
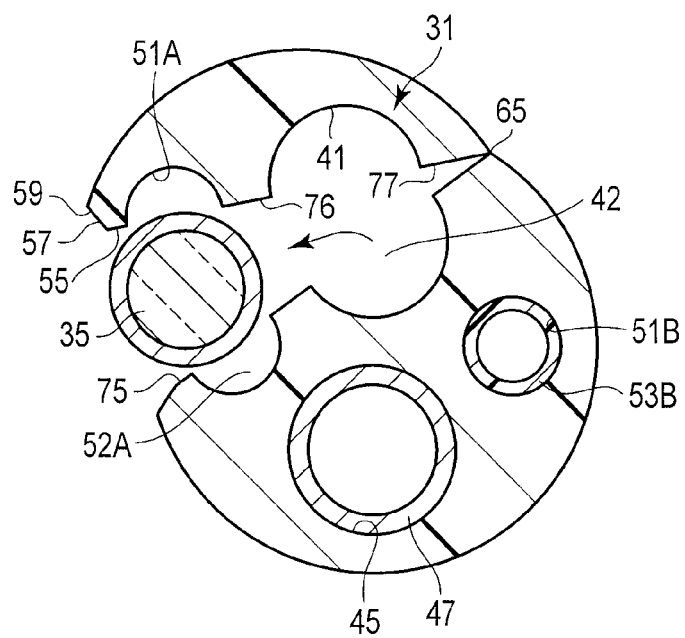
F I G. 10

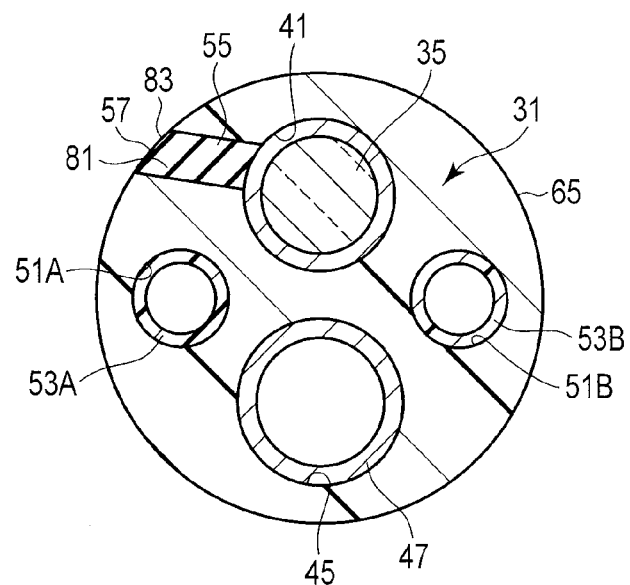
F I G. 17
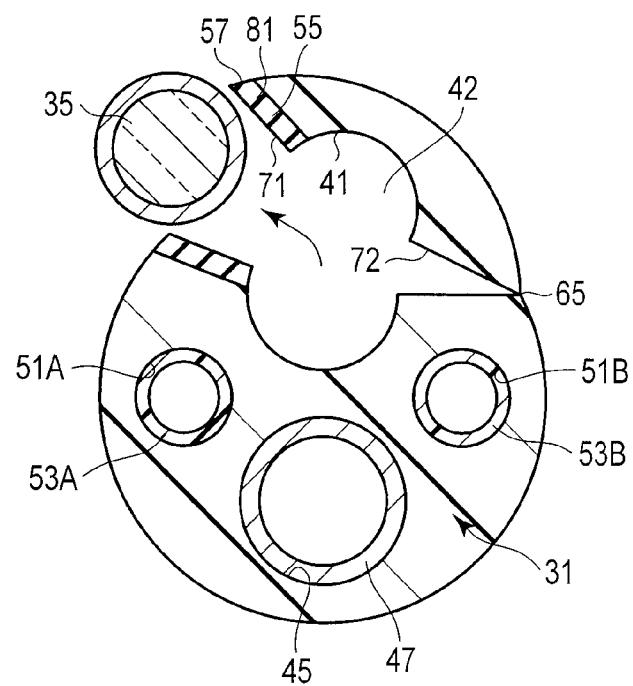
F I G. 18

ENDOSCOPE HAVING BREAKABLE PORTIONS FOR PREVENTING DAMAGE TO THE IMAGING UNIT

CROSS REFERENCE TO RELATED APPLICATIONS

This application is a Continuation Application of PCT Application No. PCT/JP2011/065190, filed Jul. 1, 2011 and based upon and claiming the benefit of priority from prior Japanese Patent Application No. 2010-203507, filed Sep. 10, 2010, the entire contents of all of which are incorporated herein by reference.

BACKGROUND OF THE INVENTION

1. Field of the Invention

The present invention relates to an endoscope including an insertion section configured to be inserted into body cavities.

2. Description of the Related Art

At a distal direction side part of an insertion section of any endoscope, a distal rigid section is provided. The distal rigid section includes a distal rigid section main body, and a functional section such as an imaging unit. The distal rigid section main body is provided with an inner peripheral surface which defines a space accommodating the functional section, and which is extended along longitudinal directions. The functional section is secured to the inner peripheral surface of the distal rigid section main body, with adhesive, screws or the like.

Jpn. Pat. Appln. KOKAI Publication No. 2003-260029 discloses an endoscope in which an imaging unit, i.e., functional section, is fixed in a distal rigid section main body with screws and filler. In this endoscope, the distal rigid section main body is made of electrically insulating material such as resin or ceramics, and an outer peripheral surface of the distal rigid section main body is electrically insulated from the imaging unit. Hence, if the endoscope is used with a high-frequency instrument, the electric current used in high-frequency treatment is prevented from flowing to the endoscope.

BRIEF SUMMARY OF THE INVENTION

According to one aspect of the invention, an endoscope includes that an insertion section configured to be inserted into a body cavity; a bending section provided to the insertion section; a distal rigid section main body provided to a part of the insertion section to a distal direction side of the bending section; a first inner peripheral surface provided to the distal rigid section main body with extending from a distal surface thereof along longitudinal directions, and defining a space in which a imaging unit is accommodated; a second inner peripheral surface provided to the distal rigid section main body with extending from the distal surface thereof along the longitudinal directions, and defining an opening through which an instrument is inserted; a first breakable portion provided between a part of an outer peripheral surface of the distal rigid section main body and the second inner peripheral surface, and including a fragile portion which is formed in a concaved-shape and which is more easy to break than any other part of the outer peripheral surface except for thereof; a second breakable portion provided between the first inner peripheral surface and the second inner peripheral surface; a third breakable portion provided between the first inner peripheral surface and a part of the outer peripheral surface of the distal rigid section main body, which differs from the fragile portion; and an envelope member covering the bending section, and also covering the outer peripheral surface of the distal rigid section main body, which includes the first breakable portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a sectional view taken along line of FIG. 2;

FIG. 4 is a perspective view schematically showing a distal rigid section main body of the endoscope according to the first embodiment;

FIG. 7 is a transverse sectional view schematically showing a distal rigid section main body of an endoscope according to a second modification of the first embodiment;

FIG. 8 is a transverse sectional view schematically explaining how to remove an imaging unit from the distal rigid section main body of the endoscope according to the second modification of the first embodiment;

FIG. 9 is a transverse sectional view schematically showing a distal rigid section main body of an endoscope according to a third modification of the first embodiment;

FIG. 10 is a transverse sectional view schematically explaining how to remove an imaging unit from the distal rigid section main body of the endoscope according to the third modification of the first embodiment;

FIG. 17 is a transverse sectional view schematically showing a distal rigid section main body of an endoscope according to a fifth modification of the second embodiment;

FIG. 18 is a transverse sectional view schematically explaining how to remove an imaging unit from the distal rigid section main body of the endoscope according to the fifth modification of the second embodiment;

DETAILED DESCRIPTION OF THE INVENTION

First Embodiment

The first embodiment of this invention will be described with reference to FIG. 1 to FIG. 5.

Figure 1:
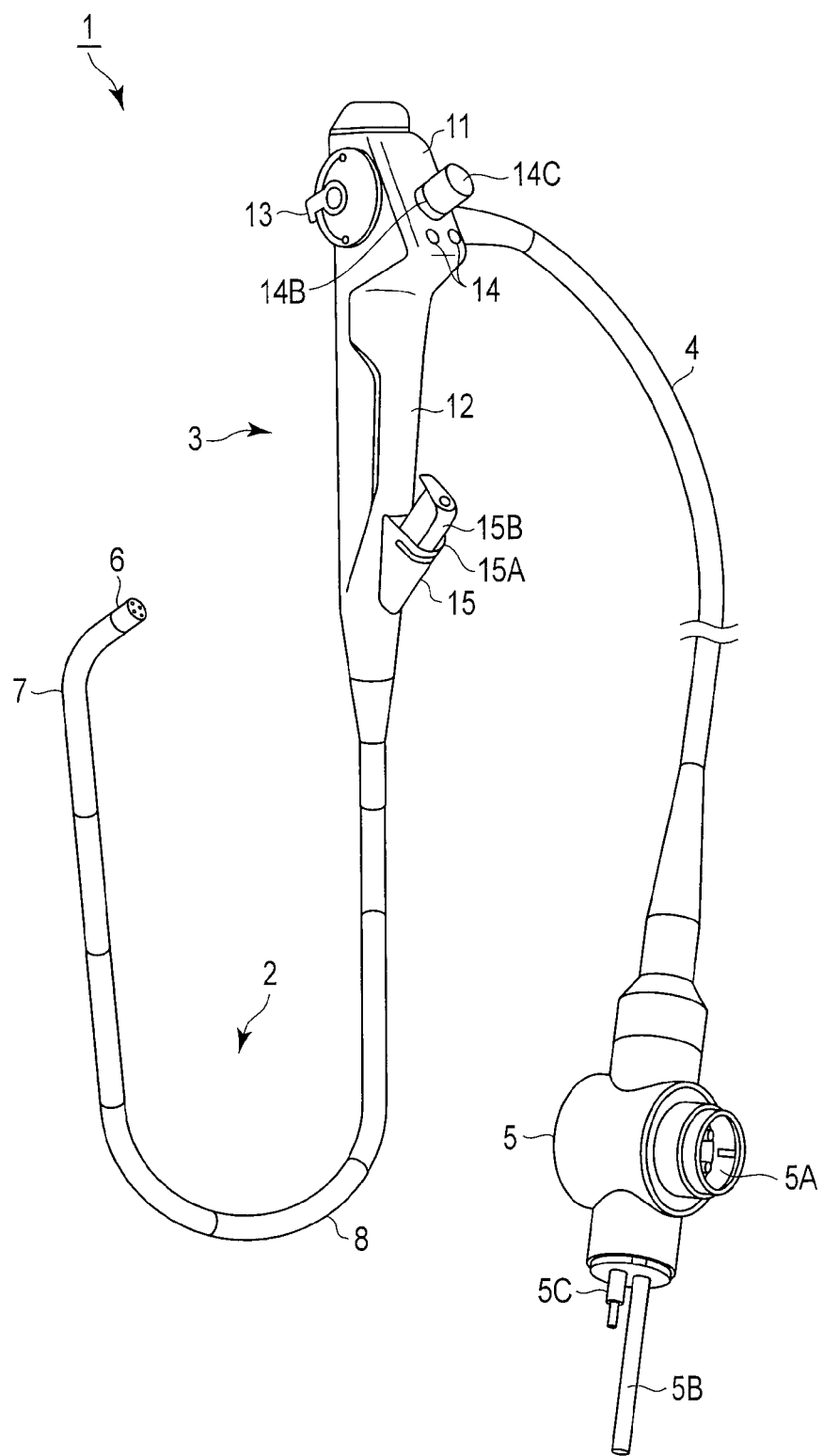
FIG. 1 is a perspective view schematically showing an endoscope according to a first embodiment of this invention.

FIG. 1 is a diagram showing an endoscope according to this embodiment. As shown in FIG. 1, the endoscope includes an insertion section 2 which is configured to be inserted into a body cavity, and which is extended in longitudinal directions, and an operation section 3 coupled to a proximal end of an insertion section 2. An universal cord 4 is connected at one end to the operation section. A scope connector is provided to the other end of the universal cord 4. The scope connector 5 includes an electrical connecting portion 5A, a light-source connecting portion 5B, and a cap 5C.

The insertion section 2 includes a distal rigid section 6 provided on a distal direction side part of the insertion section 2, a bending section 7 provided to a proximal direction side of the distal rigid section 6 and configured to perform bending motion, and an elongated flexible tubular section 8 provided to the proximal direction side of the bending section 7.

The operation section 3 includes an operation-section casing 11, and a holding-section casing 12 provided to a direction side where the insertion section 2 is located with respect to the operation-section casing 11. A bending lever 13 (bending operation section) configured to perform a bending operation of the bending section 7 is provided on the operation-section casing 11. On the operation-section casing 11, a plurality of remote switches 14 configured to perform remote control in an image processing unit (not shown) or the like are provided. A suction port 14B is provided to the operation-section casing 11. A suction button 14C is removably attached to the suction port 14B. An instrument insertion portion 15 defining an opening 15A, through which an instrument such as forceps may be inserted, is provided to the holding-part casing 12. A plug 15B, configured to close the opening 15A when any instrument is not inserted, is detachably attached to the instrument insertion portion 15.

Figure 2:
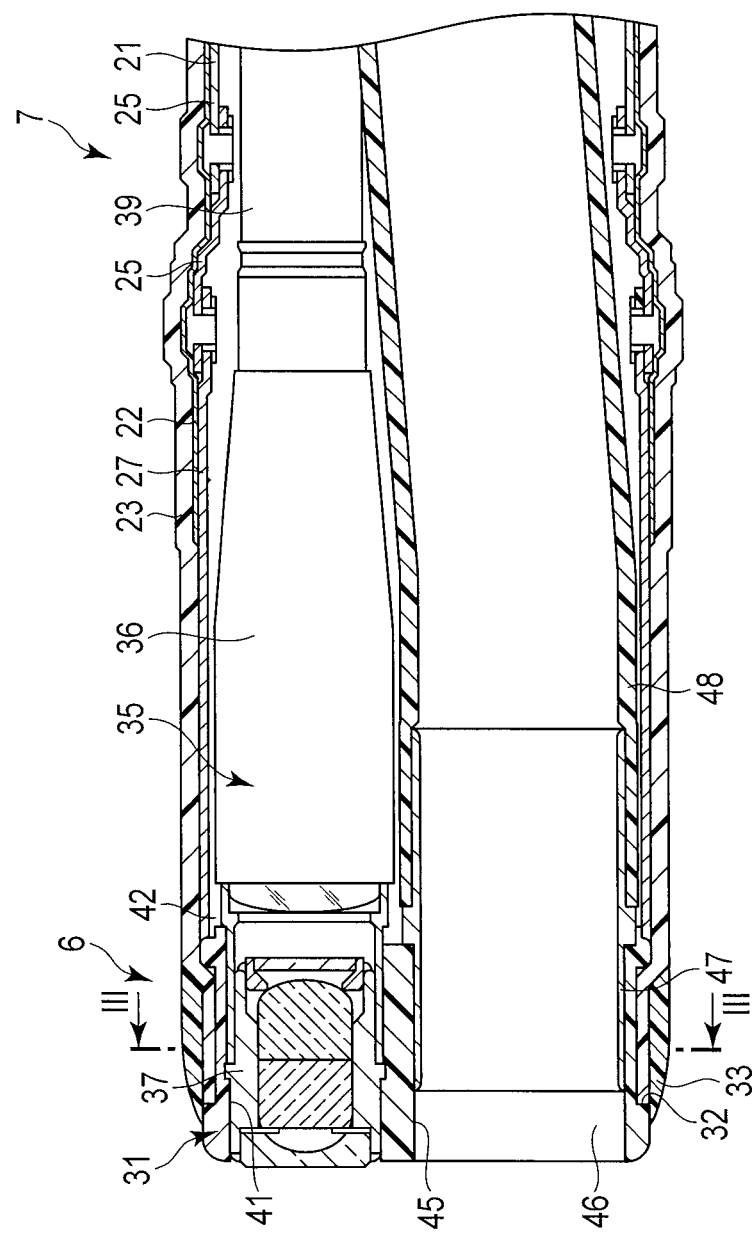
FIG. 2 is a longitudinal sectional view schematically showing an internal structure of a distal rigid section and a bending section of the endoscope according to the first embodiment.

FIG. 2 is a diagram showing an internal structure of the distal rigid section 6 and bending section 7. As shown in FIG. 2, the bending section 7 includes a metallic bending tube 21, a metallic reticular tube 22 covering an outer peripheral surface of the bending tube 21, and an envelope 23 made of resin and covering an outer peripheral surface of the reticular tube 22. The bending tube 21 is formed by juxtaposing a plurality of bending rings 25 in the longitudinal directions and coupling them together in a state that each bending rings 25 is rotatable with respect to an adjacent one.

The distal rigid section includes a distal rigid section main body 31 made of an electrically insulating material such as resin or ceramics. A most distal bending ring, which is a bending ring on the most distal direction side in the bending tube 21, is coupled to the distal rigid section main body 31. The envelope 23 extends up to a part to the distal direction side of a distal end of the reticular tube 22 in a state that the envelope 23 covers an outer peripheral surface of the distal rigid section main body 31. A step portion 32 is formed on the outer peripheral surface of the distal rigid section main body 31, and a distal end of the envelope 23 abuts on the step portion 32. A resin layer (or insulating layer) 33 made of, for example, adhesive, secures the envelope sheath 23 to the distal rigid section main body 31.

FIG. 3 is a sectional view taken along line of FIG. 2. FIG. 4 is a diagram showing the distal rigid section main body 31. As shown in FIG. 2 and FIG. 3, a imaging unit 35, which is a functional section configured to perform image pick up, is attached to the distal rigid section main body 31. The imaging unit 35 includes an imaging section 36 provided with imaging elements, and an observation optical system 37 configured to guide an object image to the imaging section 36. As shown in FIG. 2 to FIG. 4, the distal rigid section main body 31 includes a first inner peripheral surface 41 extended from a distal surface of the distal rigid section main body 31 and defining a first space 42 in which the imaging unit 35 is accommodated. The observation optical system 37 is secured to the first inner peripheral surface 41 with, for example, adhesive. The imaging unit 35 is thereby attached to the distal rigid section main body 31.

An imaging cable 39 is connected at one end to the imaging section 36 of the imaging unit 35. The imaging cable 39 is extended toward the proximal direction through an inside of the bending tube 21 and an inside of the flexible tubular section 8. The imaging cable 39 further extends through an inside of the operation section 3 and an inside of the universal cord 4, and is connected, at the other end, to the image processing unit (not shown) by the electrical connector portion 5A of the scope connector 5.

As shown in FIG. 2 to FIG. 4, the distal rigid section main body 31 includes a second inner peripheral surface 45 extended in the longitudinal directions from the distal surface of the distal rigid section main body 31 with being spaced from the first inner peripheral surface 41 in directions perpendicular to the longitudinal directions. The second inner peripheral surface 45 defines a second space 46. A tube connecting pipe 47 is coupled at one end to the second inner peripheral surface 45, and the second space 46 communicates with an interior of the tube connecting pipe 47. The tube connecting pipe 47 is coupled, at the other end, to one end of an instrument insertion tube 48, through which an instrument such as forceps is configured to be inserted. The instrument insertion tube 48 is extended toward the proximal direction through the inside of the bending tube 21 and the inside of the flexible tubular section 8, and is branched into two parts in the operation section 3. One branched part of the instrument insertion tube 48 is connected to the instrument insertion portion 15. The other branched part of the instrument insertion tube 48 is connected to the suction port 14B of the operation-section casing 11. A suction tube (not shown) is connected at one end to the suction port 14B via the suction button. The other end of the suction tube is connected to a suction unit (not shown).

As shown in FIG. 3 and FIG. 4, the distal rigid section main body 31 includes a third inner peripheral surface 51A and a fourth inner peripheral surface 51B each of which is extend from the distal surface of the distal rigid section main body 31 in the longitudinal directions with being spaced apart in the directions perpendicular to the longitudinal directions from the first inner peripheral surface 41 and second inner peripheral surface 45. The third peripheral surface 51A and fourth peripheral surface 51B are arranged with being spaced apart from each other in the directions perpendicular to the longitudinal directions. The third peripheral surface 51A defines a third space 52A, and the fourth peripheral surface 51B defines a fourth space 52B. A first light guide 53A is connected at one end to the third peripheral surface 51A, and a second light guide 53B is connected at one end to the fourth peripheral surface 51B, respectively. Therefore, the third space 52A communicates with an interior of the first light guide 53A, and the fourth space 52B communicates with an interior of the second light guide 53B. The light guides 53A and 53B are extended toward the proximal direction through the inside of the bending tube 21 and the inside of the flexible tubular section 8. Passing through the inside of the operation section 3 and the inside of the universal cord 4, the light guides 53A and 53B are connected at the other end to a light source unit (not shown) via the light-source connecting portion 5B of the scope connector 5. The light guides 53A and 53B are configured to guide the light emitted from the light source unit, and the guided light is irradiated to an object through an observation window (not shown).

As shown in FIG. 3 and FIG. 4, the distal rigid section main body 31 includes a fragile portion 55. The fragile portion 55 is formed to be more easily broken than any other part of the distal rigid section main body 31 except for the fragile portion 55. The fragile portion 55 includes a first outer-peripheral exposed portion 57 which is extended along the longitudinal directions with being exposed on the outer peripheral of the distal rigid section main body 31. The fragile portion 55 is extended from the first outer-peripheral exposed portion 57 toward the first inner peripheral surface 41.

The fragile portion 55 includes a groove (first groove) 59 which is extended along the longitudinal directions in the first outer-peripheral exposed portion 57, and which concaves toward an inner peripheral direction from the outer peripheral surface of the distal rigid section main body 31. The fragile portion 55 further includes the second inner peripheral surface 45 which defines the second space 46. The second inner peripheral surface 45 is positioned between the first outer-peripheral exposed portion 57 and the first inner peripheral surface 41 in the directions perpendicular to the longitudinal directions.

Figure 5:
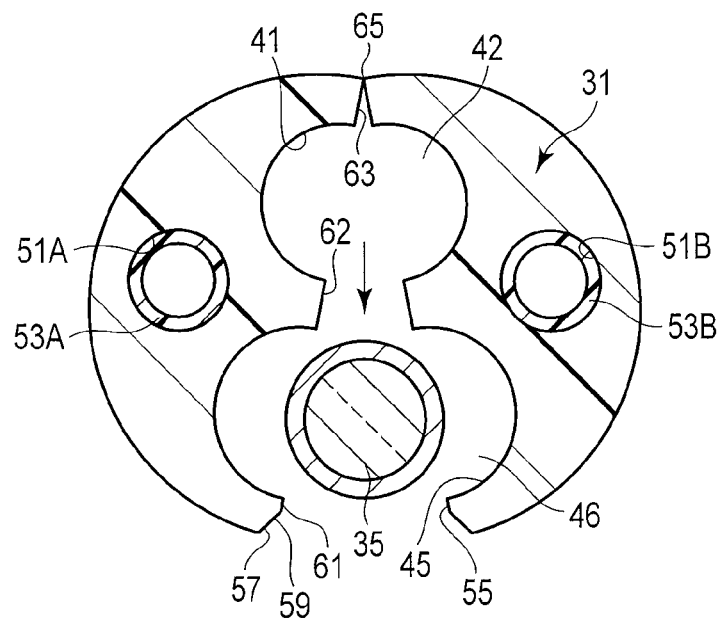
FIG. 5 is a transverse sectional view schematically explaining how to remove an imaging unit from the distal rigid section main body of the endoscope according to the first embodiment.

FIG. 5 is a diagram explaining how the imaging unit 35 is removed from the distal rigid section main body 31. As shown in FIG. 5, in the distal rigid section main body 31, a first breakable portion 61 is extended from the first outer-peripheral exposed portion 57 to the second inner peripheral surface 45 along the directions perpendicular to the longitudinal directions. The first breakable portion 61 is initially broken when the imaging unit 35, i.e., functional section, is removed, after use, from the distal rigid section main body 31. Further, in the distal rigid section main body 31, a second breakable portion 62 is extended from the second inner peripheral surface 45 to the first inner peripheral surface 41 along the directions perpendicular to the longitudinal directions. The second breakable portion 62 is broken after breaking the first breakable portion 61 when the imaging unit 35, i.e., functional section, is removed from the distal rigid section main body 31.

The distal rigid section main body 31 includes a second outer-peripheral exposed portion 65 which is exposed on the outer peripheral of the distal rigid section main body 31 at a position spaced apart from the first outer-peripheral exposed portion 57 in circumferential directions of the distal rigid section main body 31. Here, a third breakable portion 63 is extended from the first inner peripheral surface 41 to the second outer-peripheral exposed portion 65 along the directions perpendicular to the longitudinal directions. The third breakable portion 63 is broken after breaking the second breakable portion 62 when the imaging unit 35, i.e., functional section, is removed from the distal rigid section main body 31.

A function of the endoscope 1 according to this embodiment will be explained. The fragile portion 55 of the distal rigid section main body 31 includes the groove 59 and the second inner peripheral surface 45, and therefore is broken more easily than any other part of the distal rigid section main body 31 except for the fragile portion 55. Providing the fragile portion 55 which is easy to break to the distal rigid section main body 31, the distal rigid section main body 31 can be broken without exerting a relatively large load to thereof, while removing the imaging unit 35 from the distal rigid section main body 31. This reduces the load acting the imaging unit 35 when the distal rigid section main body 31 is broken.

When the distal rigid section main body 31 is broken, the first breakable portion 61, which is extended from the first outer-peripheral exposed portion 57 to the second inner peripheral surface 45, is broken at first. When the second breakable portion 62, which is extended from the second inner peripheral surface 45 to the first inner peripheral surface 41, is broken, and the third breakable portion 63, which is extended from the first inner peripheral surface 41 to the second outer-peripheral exposed portion 65, is broken, in this order, the imaging unit 35 is removed from the distal rigid section main body 31. Namely, the first breakable portion 61, which is remote from the imaging unit 35 by relatively large distance in the directions perpendicular to the longitudinal directions, is broken first. The second and third breakable portions 62 and 63, which are remote from the imaging unit 35 by relatively small distance in directions perpendicular to the longitudinal directions, are broken in a state that the first breakable portion 61 has been broken. The second and third breakable portions 62 and 63 can therefore be broken without being applied with a large load. Hence, the load exerted on the imaging unit 35 at the time of breaking the distal rigid section main body 31 is reduced.

The endoscope 1 configured as described above is advantageous as follow. In the endoscope 1, because the fragile portion 55 of the distal rigid section main body 31 includes the groove 59 and the second inner peripheral surface 45, the fragile portion 55 can be more easily broken than any other part of the distal rigid section main body 31 except for the fragile portion 55. Providing the fragile portion 55 which is easy to break, the distal rigid section main body 31 can therefore be broken without applying a large load to the distal rigid section main body 31 when the imaging unit 35 is removed by breaking the distal rigid section main body 31. This reduces the load applied to the imaging unit 35 when the distal rigid section main body 31 is broken. The imaging unit 35 can therefore hardly be broken when the imaging unit 35 is removed from the distal rigid section main body 31.

When the imaging unit 35 is removed from the distal rigid section main body 31 in the endoscope 1, the first breakable portion 61, which is remote from the imaging unit 35 by relatively large distance in the directions perpendicular to the longitudinal directions, is first broken. After the first breakable portion 61 has been broken, the second breakable portion 62 and the third breakable portion 3, which are remote from the imaging unit 35 by relatively small distance in directions perpendicular to the longitudinal directions, are broken. The second and third breakable portions 62 and 63 can therefore be broken without being exerted with a large load. In other words, the imaging unit 35 receives a further smaller load when the distal rigid section main body 31 is broken. Thus, the imaging unit 35 is hardly broken when imaging unit 35 is removed from the distal rigid section main body 31.

Modifications of the First Embodiment

Figure 6:
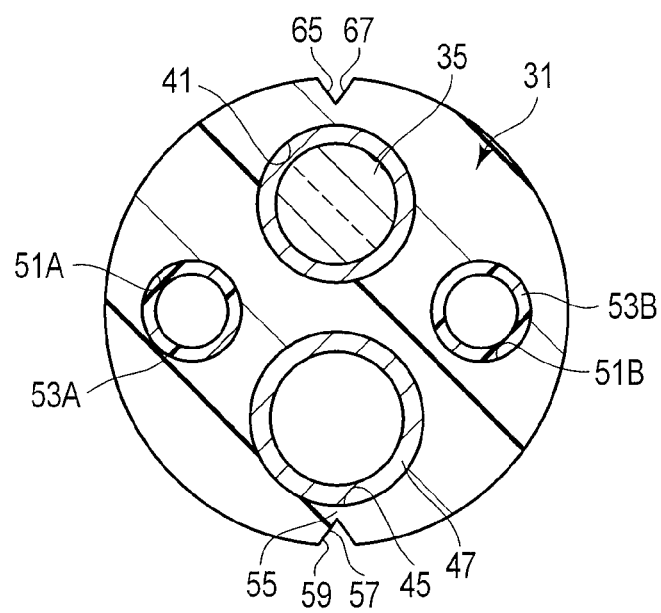
FIG. 6 is a transverse sectional view schematically showing a distal rigid section main body of an endoscope according to a first modification of the first embodiment.

In a first modification of the first embodiment, the distal rigid section main body 31 may include a groove (second groove) 67 which is extended in the second outer-peripheral exposed portion 65 along the longitudinal directions, and which concaves toward the inner peripheral direction from the outer peripheral surface of the distal rigid section main body 31, as shown in FIG. 6. The groove 67 causes to break the third breakable portion 63 with a further smaller load, at the time of removing the imaging unit 35 from the distal rigid section main body 31.

In a second modification of the first embodiment, the fragile portion 55 does not include a second inner peripheral surface 45, as seen from FIG. 7, though it includes a groove 59 in the first outer-peripheral exposed portion 57. That is, in this modification, the second inner peripheral surface 45 is not arranged between the first outer-peripheral exposed portion 57 and the first inner peripheral surface 41 in the directions perpendicular to the longitudinal directions.

In this modification, a first breakable portion 71 is extended, as shown in FIG. 8, from the first outer-peripheral exposed portion 57 to the first inner peripheral surface 41 along the directions perpendicular to the longitudinal directions. Further, a second breakable portion 72 is extended from the first inner peripheral surface 41 to the second outer-peripheral exposed portion 65 in the directions perpendicular to the longitudinal directions. The second outer-peripheral exposed portion 65 is spaced apart from the first outer-peripheral exposed portion 57 in the circumferential directions of the distal rigid section main body 31. To remove the imaging unit 35 from the distal rigid section main portion 31, the first breakable portion 71 is broken first, and the second breakable portion 72 is then broken. The imaging unit 35 is thereby removed from the distal rigid section main body 31.

In a third modification of the first embodiment, the fragile portion 55 includes, as shown in FIG. 9, a groove 59 provided to the first-peripheral exposed portion 57, and a third inner peripheral surface 51A. That is, in this modification, the third inner peripheral surface 51A is positioned between the first outer-peripheral exposed portion 57 and the first inner peripheral surface 41 in the directions perpendicular to the longitudinal directions.

In this modification, a first breakable portion 75 is provided, as shown in FIG. 10, from the first outer-peripheral exposed portion 57 to the third inner peripheral surface 51A along the directions perpendicular to the longitudinal directions. Further, a second breakable portion 76 is extended from the third inner peripheral surface 51A to the first inner peripheral surface 41 along the directions perpendicular to the longitudinal directions. Still further, a third breakable portion 77 is extended from the first inner peripheral surface 41 to the second outer-peripheral exposed portion 65 in the directions perpendicular to the longitudinal directions. The second outer-peripheral exposed portion 65 is spaced apart from the first outer-peripheral exposed portion 57 in the circumferential directions of the distal rigid section main body 31. To remove the imaging unit 35 from the distal rigid section main body 31, the first breakable portion 75 is broken first. Further the second breakable portion 76 and the third breakable part 77 is then broken in this order, and the imaging unit 35 is thereby removed.

The fourth peripheral surface 51B may be located between the first outer-peripheral exposed portion 57 and the first inner peripheral surface 41 in the directions perpendicular to the longitudinal directions. Further, the fragile portion 55 may include a groove 59 provided to the first outer-peripheral exposed portion 57, and the fourth peripheral surface 51B. That is, the fragile portion 55 only needs to include a groove 59 provided to the first outer-peripheral exposed portion 57, and a second inner peripheral surface (i.e., second inner peripheral surface 45 in the first embodiment, and third inner peripheral surface 51A in the third modification) which is provided between the first outer-peripheral exposed portion 57 and the first inner peripheral surface 41 with being spaced apart from the first inner peripheral surface 41 in the directions perpendicular to the longitudinal directions, and which is extended from the distal surface of the distal rigid section main body 31 along the longitudinal directions, the second inner peripheral surface defining the second space (i.e., second space 46 in the first embodiment, and third space 52A in the third modification) different from the first space 42.

Second Embodiment

A second embodiment of this invention will be described with reference to FIG. 11 and FIG. 12. In the second embodiment, the distal rigid section main body 31 is modified as will be described below. The same parts and the same functional parts as those according to the first embodiment are provided with the same reference marks and are not described.

Figure 11:
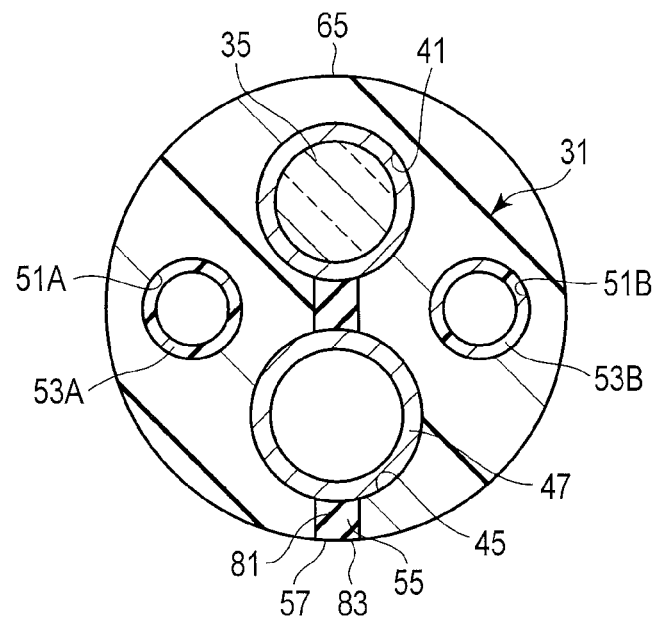
FIG. 11 is a transverse sectional view schematically showing a distal rigid section main body of an endoscope according to a second embodiment of this invention.

FIG. 11 is a diagram showing the distal rigid section main body 31 according to this embodiment. As shown in FIG. 11, the distal rigid section main body 31 includes a fragile portion 55 as in the first embodiment. The fragile portion 55 includes a second inner peripheral surface 45, and a fragile member (first fragile member) 81 extended from the first outer-peripheral exposed portion 57 toward the first inner peripheral surface 41. The fragile member 81 is made of material, such as rubber, which is less strong than the material (i.e., resin or ceramics) of any other part of the distal rigid section main body 31 except for the fragile member 81. The fragile member 81 is extended from the first outer-peripheral exposed portion 57 to the first inner peripheral surface 41, passing through the second inner peripheral surface 45. The second inner peripheral surface 45 is located between the first outer-peripheral exposed portion 57 and the first inner peripheral surface 41, as in the first embodiment, in the directions perpendicular to the longitudinal directions. An index 83 may be provided, by marking, on the first outer-peripheral exposed portion 57.

Figure 12:
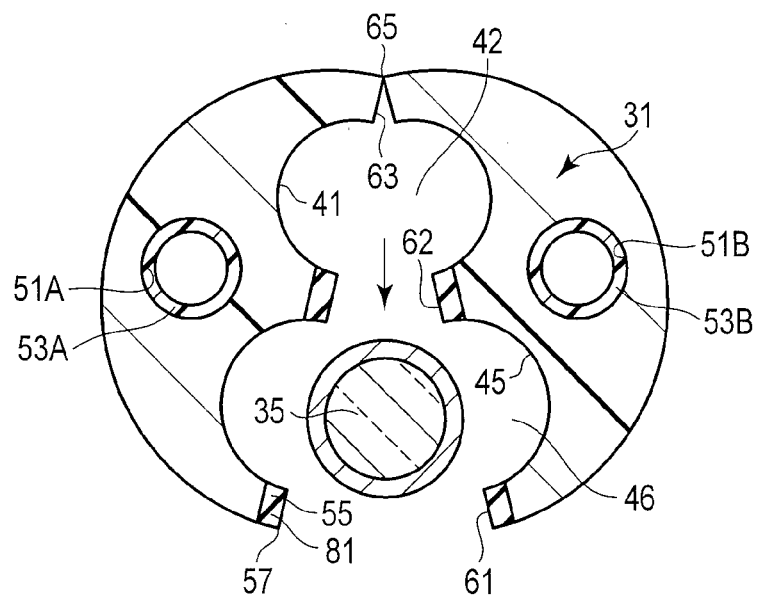
FIG. 12 is a transverse sectional view schematically explaining how to remove an imaging unit from the distal rigid section main body of the endoscope according to the second embodiment.

FIG. 12 is a diagram explaining how to remove the imaging unit 35 from the distal rigid section main body 31. As shown in FIG. 12, a first breakable portion 61 is extended from the first outer-peripheral exposed portion 57 to the second inner peripheral surface 45 along the directions perpendicular to the longitudinal directions. Further, a second breakable portion 62 is extended from the second inner peripheral surface 45 to the first inner peripheral surface 41 along the directions perpendicular to the longitudinal directions. Still further, a third breakable portion 63 is extended from the third breakable portion 63 to the second outer-peripheral exposed portion 65 along the directions perpendicular to the longitudinal directions. In order to remove the imaging unit 35 from the distal rigid section main body 31, the first breakable portion 61 is broken first from the first outer-peripheral exposed portion 57, using the index 83 as a marker. The second breakable portion 62 and third breakable portion 63 are then broken in the order they are mentioned, the camera unit 35 is thereby removed from the distal rigid section main body 31. As shown in FIG. 12, the first breakable portion 61 and second breakable portion 62 are formed on the fragile member 81. Nonetheless, the first breakable portion 61 and second breakable portion 62 may be formed at a boundary between the fragile member 81 and any part of the distal rigid section main body 31 other than the fragile member 81.

The endoscope 1 configured as described above is advantageous in the following respect. That is, as the fragile portion 55 includes the fragile member 81 and the second inner peripheral surface 45, the fragile portion 55 can be more easily broken than any other part of the distal rigid section main body 31 except for the fragile portion 55, in the endoscope 1. Moreover, providing the fragile part 55 easy to break to the distal rigid section main body 31, the distal rigid section main body 31 can be broken without applying a large load thereto when the distal rigid section main body 31 is broken to remove the imaging unit 35. That is, the load exerted on the imaging unit 35 at the time of breaking the distal rigid section main body 31 is small. Hence, the imaging unit 35 is hardly damaged as the imaging unit 35 is removed from the distal rigid section main body.

In the endoscope 1, the distal rigid section main body 31 is broken first at the first breakable portion 61, which is remote from the imaging unit 35 by relatively large distance in the directions perpendicular to the longitudinal directions, when the imaging unit 35 is removed from the distal rigid section main body 31. In the state that the first breakable portion 61 has been broken, the second breakable portion 62 and third breakable portion 63 are broken, which are remote from the imaging unit 35 by relatively small distance in the directions perpendicular to the longitudinal directions. The second breakable portion 62 and third breakable portion 63 are thus broken without the necessity applying a large load to them. That is, the load applied to the imaging unit 35 at the time of breaking the distal rigid section main body 31 is further smaller. The imaging unit 35 can be more hardly broken when the imaging unit 35 is removed from the distal rigid section main body 31.

Modifications of the Second Embodiment

Figure 13:
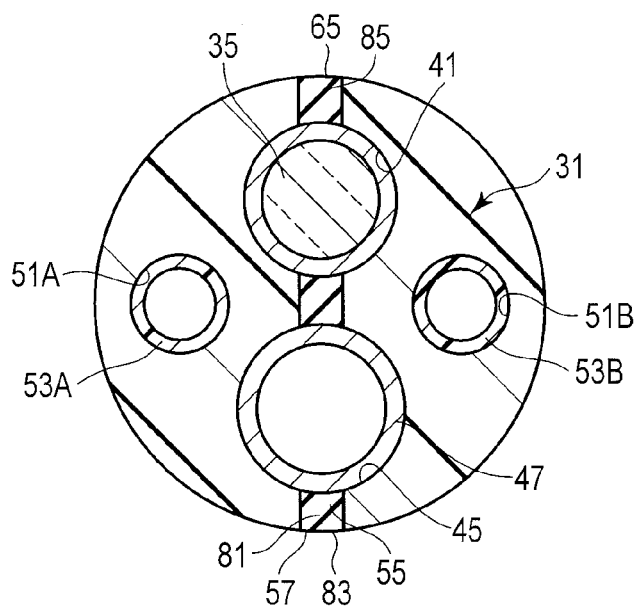
FIG. 13 is a transverse sectional view schematically showing a distal rigid section main body of an endoscope according to a first modification of the second embodiment.

In a first modification of the second embodiment, the distal rigid section main body 31 includes a fragile member (second fragile member) 85 extended from the first inner peripheral surface 41 to the second outer-peripheral exposed portion 65 along the directions perpendicular to the longitudinal directions, as shown in FIG. 13. Like the fragile member 81, the fragile member 85 is made of material, such as rubber, which is less strong than the material of any parts of the distal rigid section main body 31 except for the fragile members 81 and 85. The third breakable portion 63 can therefore be broken with a further smaller load at the time of removing the imaging unit 35 from the distal rigid section main body 31.

Figure 14:
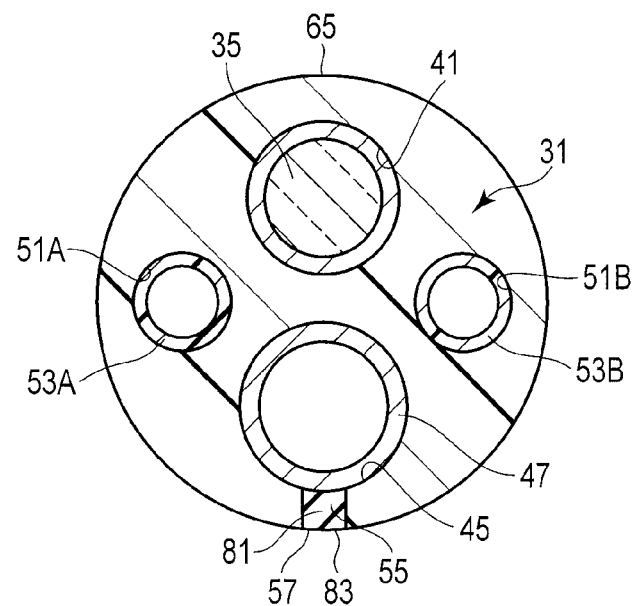
FIG. 14 is a transverse sectional view schematically showing a distal rigid section main body of an endoscope according to a second modification of the second embodiment.
Figure 15:
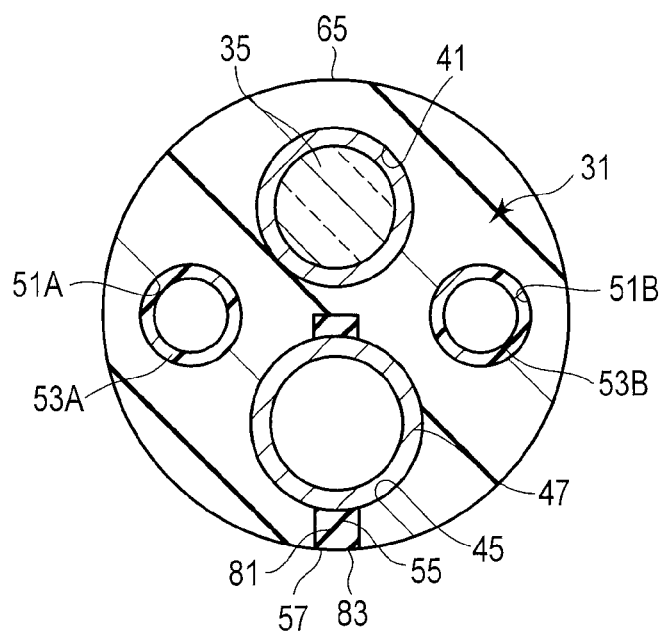
FIG. 15 is a transverse sectional view schematically showing a distal rigid section main body of an endoscope according to a third modification of the second embodiment.
Figure 16:
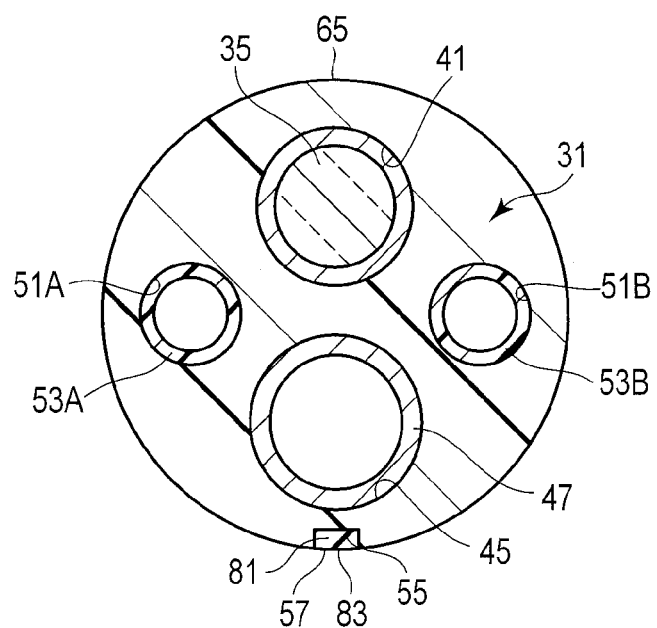
FIG. 16 is a transverse sectional view schematically showing a distal rigid section main body of an endoscope according to a fourth modification of the second embodiment.

In a second modification of the second embodiment, the fragile member 81 is extended, as shown in FIG. 14, from the first outer-peripheral exposed part 57 to the second inner peripheral surface 45 along the directions perpendicular to the longitudinal directions. Similarly, in a third modification of the second embodiment, the fragile member 81 is extended, as shown in FIG. 15, from the first outer-peripheral exposed portion 57 to a part between the second inner peripheral surface 45 and the first inner peripheral surface 41. Further, in a fourth modification of the second embodiment, the fragile member 81 is extended, as shown in FIG. 16, from the first outer-peripheral exposed portion 57 to a part between the first outer-peripheral exposed portion 57 and the second inner peripheral surface 45. That is, in the second to fourth modifications of the second embodiment, the fragile member 81 is extended from the first outer-peripheral exposed portion 57 toward the first inner peripheral surface 41.

In a fifth modification of the second embodiment, the fragile portion 55 does not include the second inner peripheral surface 45, and includes only the fragile member 81 extended, as shown in FIG. 17, from the first outer-peripheral exposed portion 57 toward the first inner peripheral surface 41. Thus, in this modification, the second inner peripheral surface 45 is not located between the first outer-peripheral exposed part 57 and the first inner peripheral surface 41 in the directions perpendicular to the longitudinal directions.

In this modification, a first breakable portion 71 is extended, as shown in FIG. 18, from the first outer-peripheral exposed portion 57 to the first inner peripheral surface 41 along the directions perpendicular to the longitudinal directions. Further, a second breakable portion 72 is extended from the first inner peripheral surface 41 to the second outer-peripheral exposed portion 65 along the directions perpendicular to the longitudinal directions. The second outer-peripheral exposed portion 65 is spaced apart from the first outer-peripheral exposed portion 57 in the circumferential directions of the distal rigid section main body 31. When the imaging unit 35 is removed from the distal rigid section main body 31, the first breakable portion 71 is broken first, and the second breakable portion 72 is then broken. The imaging unit 35 is thereby removed.

Figure 19:
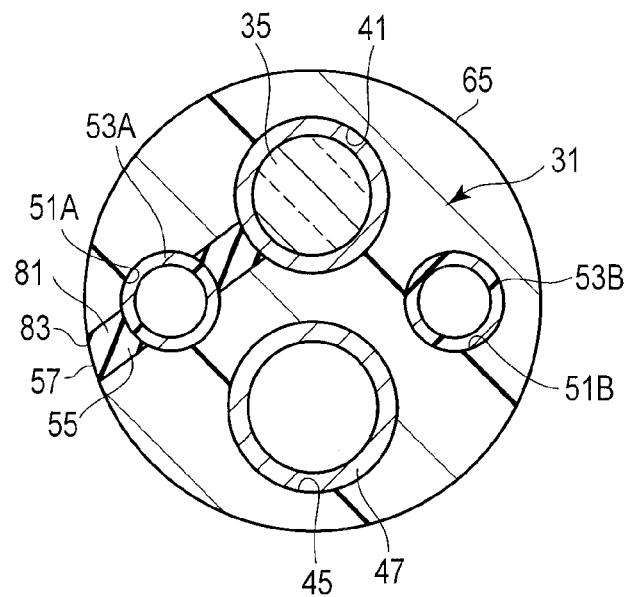
FIG. 19 is a transverse sectional view schematically showing a distal rigid section main body of an endoscope according to a sixth modification of the second embodiment.

In a sixth modification of the second embodiment, the fragile portion 55 includes, as shown in FIG. 19, a fragile member 81 extended from the first outer-peripheral exposed portion 57 toward the first inner peripheral surface 41, and a third inner peripheral surface 51A. That is, the third inner peripheral surface 51A is located between the first outer-peripheral exposed portion 57 and the first inner peripheral surface 41 in the directions perpendicular to the longitudinal directions.

Figure 20:
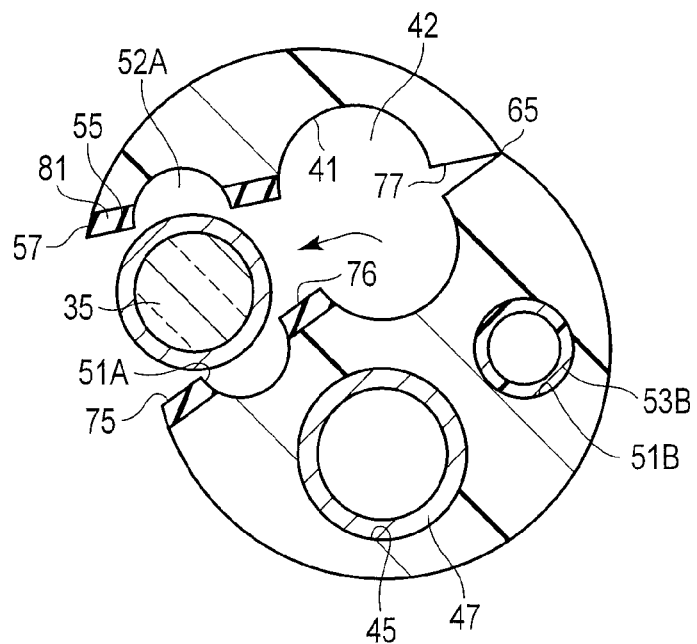
FIG. 20 is a transverse sectional view schematically explaining how to remove an imaging unit from the distal rigid section main body of the endoscope according to the sixth modification of the second embodiment.

In this modification, a first breakable portion 75 is provided, as shown in FIG. 20, from the first outer-peripheral exposed portion 57 to the third inner peripheral surface 51A along the directions perpendicular to the longitudinal directions. Further, a second breakable portion 76 is provided from the third inner peripheral surface 51A to the first inner peripheral surface 41 along the directions perpendicular to the longitudinal directions. Still further, a third breakable portion 77 is provided from the first inner peripheral surface 41 to the second outer-peripheral exposed portion 65 in the directions perpendicular to the longitudinal directions. The second outer-peripheral exposed portion 65 is spaced apart from the first outer-peripheral exposed portion 57 in the circumferential directions of the distal rigid section main body 31. At the time of removing the imaging unit 35 from the distal rigid section main body 31, the first breakable portion 75 is broken first. The second breakable portion 76 and the third breakable portion 77 are broken in this order, and the imaging unit 35 is thereby removed.

The fourth peripheral surface 51B may be located between the first outer-peripheral exposed portion 57 and the first inner peripheral surface 41 in the directions perpendicular to the longitudinal directions. Further, the fragile portion 55 may include a fragile member 81 extended from the first outer-peripheral exposed portion 57 toward the first inner peripheral surface 41, and a fourth inner peripheral surface 51B. That is, the fragile portion 55 only needs to include the fragile member 81 extended from the first outer-peripheral exposed portion 57 toward the first inner peripheral surface 41, and a second inner peripheral surface (i.e., second inner peripheral surface 46 in the second embodiment, and third inner peripheral surface 52A in the sixth modification) which is provided between the first outer-peripheral exposed portion 57 and the first inner peripheral surface 41 with being spaced apart from the first inner peripheral surface 41 in the directions perpendicular to the longitudinal directions, which is extended from the distal surface of the distal rigid section main body 31 along the longitudinal directions, the second inner peripheral surface defining the second space (i.e., second space 46 in the second embodiment, and third space 52A in the sixth modification) different from the first space 42.

Other Modifications

Figure 21:
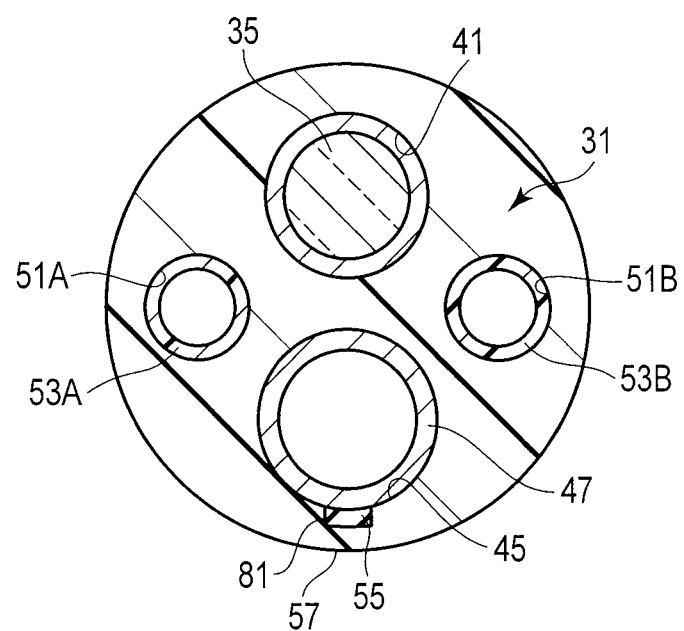
FIG. 21 is a transverse sectional view schematically showing a distal rigid section main body of an endoscope according to a referential example of the present invention.

In the embodiments and the various modifications thereof all described above, the parts of the distal rigid section main body 31 other than the fragile members 81 and 85 are made of electrically insulating material, such as resin and ceramics. Nonetheless, they may be made of, for example, electrically conductive metal. Further, as in a referential example shown in FIG. 21, the fragile member 81 may be extended from a part between the first outer-peripheral exposed portion 57 and the second inner peripheral surface 45 to the second inner peripheral surface 45. A fragile portion 55, which can be more easily broken than any other parts of the distal rigid section main body 31, is therefore formed.

Further, an air/water supplying nozzle configured to supply air and water to any affected part may be attached to the distal rigid section main body 31. In this case, the distal rigid section main body 31 includes an inner peripheral surface which is extended from the distal surface of the distal rigid section main body 31 and which defines a space communicating with an interior of the air/water supplying nozzle, the air/water supplying nozzle being coupled to the inner peripheral surface. The inner peripheral surface, to which the air/water supplying nozzle is coupled, may be arranged between the first outer-peripheral exposed portion 57 and the first inner peripheral surface 41 in the directions perpendicular to the longitudinal directions. If this is the case, the inner peripheral surface, to which the air/water supplying nozzle is coupled, constitutes a part of the fragile portion 55.

In the embodiments and the modifications thereof all described above, the imaging unit 35 is accommodated in the first space 42 defined by the first inner peripheral surface 41. The functional section is not limited thereto, nevertheless. A light emitting member, such as an LED, configured to illuminate an object may be accommodated, as functional section, in the first space 42. In this case, the light emitting member is hardly damaged when it is removed from the distal rigid section main body 31, as in the embodiments and the modifications thereof all described above.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
    an insertion section configured to be inserted into a body cavity;
    a bending tube provided to the insertion section and including a plurality of bending rings;
    a distal rigid section main body provided to a part of the insertion section and located on a distal side with respect to the bending tube;
    a first inner peripheral surface provided to the distal rigid section main body, the first inner peripheral surface extending from a distal surface of the distal rigid section main body along a longitudinal direction, the first inner peripheral surface defining a first space inside the distal rigid section main body;
    an imaging unit configured to pick up an image, the imaging unit being disposed in the first space;
    a second inner peripheral surface provided to the distal rigid section main body, the second inner peripheral surface extending from the distal surface of the distal rigid section main body along the longitudinal direction, the second inner peripheral surface defining a second space inside the distal rigid section main body;
    a concave shaped groove formed at a first location on an outer peripheral surface of the distal rigid section main body to define a first breakable portion between the groove and the second inner peripheral surface, the groove continuously extending from the distal surface to a proximal surface of the distal rigid section main body, a proximal end of the groove being located at the proximal surface of the distal rigid section main body, a concave shape of the groove being constant from a distal end of the groove to the proximal end of the groove;
    a second breakable portion provided between the first inner peripheral surface and the second inner peripheral surface;
    a third breakable portion provided between the first inner peripheral surface and a second location on the outer peripheral surface of the distal rigid section main body, the second location differing from the first location; and
    an envelope member covering the bending tube, and also covering the outer peripheral surface of the distal rigid section main body, which includes the first breakable portion,
    wherein the first breakable portion is easier to break than the second and third breakable portions such that a force applied to break the first breakable portion is not directly applied to the imaging unit.

2. The endoscope of claim 1, wherein the concave shaped groove has a v-shape to facilitate breaking.

3. The endoscope of claim 1, wherein an amount of material to be broken in the first breakable portion is less than an amount of material to be broken in the second or third breakable portions.

4. The endoscope of claim 1, wherein the second space is disposed between the groove and the first space.

5. An endoscope comprising:
    an insertion section configured to be inserted into a body cavity;
    a bending tube provided to the insertion section and including a plurality of bending rings;
    a distal rigid section main body provided to a part of the insertion section and located on a distal side with respect to the bending tube;
    a first inner peripheral surface provided to the distal rigid section main body, the first inner peripheral surface extending from a distal surface of the distal rigid section main body along a longitudinal direction, the first inner peripheral surface defining a first space inside the distal rigid section main body;

an imaging unit configured to pick up an image, the imaging unit being disposed in the first space;

a second inner peripheral surface provided to the distal rigid section main body, the second inner peripheral surface extending from the distal surface of the distal rigid section main body along the longitudinal direction, the second inner peripheral surface defining a second space inside the distal rigid section main body;

a concave shaped groove formed at a first location on an outer peripheral surface of the distal rigid section main body to define a first breakable portion between the groove and the second inner peripheral surface, the groove continuously extending from the distal surface to a proximal surface of the distal rigid section main body, a proximal end of the groove being located at the proximal surface of the distal rigid section main body, a concave shape of the groove being constant from a distal end to the proximal end in the groove;

a second breakable portion provided between the first inner peripheral surface and the second inner peripheral surface;

a third breakable portion provided between the first inner peripheral surface and a second location on the outer peripheral surface of the distal rigid section main body, the second location differing from the first location; and an envelope member covering the bending tube, and also covering the outer peripheral surface of the distal rigid section main body, which includes the first breakable portion, wherein an amount of material to be broken in the first breakable portion is less than an amount of material to be broken in each of the second and third breakable portions.

* * * * *